United States Patent [19]

Drake

[11] 4,440,953

[45] Apr. 3, 1984

[54] PURIFICATION OF N-SUBSTITUTED AMINOBENZALDEHYDES

[75] Inventor: Charles A. Drake, Bartlesville, Okla.

[73] Assignee: Phillips Petroleum Company, Bartlesville, Okla.

[21] Appl. No.: 489,447

[22] Filed: Apr. 28, 1983

[51] Int. Cl.³ .............................................. C07C 85/26
[52] U.S. Cl. ..................................... 564/437; 564/438
[58] Field of Search ................................. 564/437, 438

[56] References Cited

U.S. PATENT DOCUMENTS

| 961,915 | 6/1910 | Vagt | 564/438 X |
| 3,126,413 | 3/1964 | Zimmerman | 564/437 |
| 3,536,593 | 10/1970 | Hurley et al. | 564/437 X |
| 3,882,181 | 5/1975 | Forster | 564/437 X |

OTHER PUBLICATIONS

*Chem. Abstracts,* par. 64:1933 (1966).
*Org. Syn. Coll.,* vol. 1, (1941), pp. 214–217.
*Org. Syn.,* vol. 33, (1953), pp. 27–29.

Primary Examiner—Paul F. Shaver

[57] ABSTRACT

The purification of N-substituted aminobenzaldehydes, such as p-dimethylaminobenzaldehyde, is facilitated via the use of sequential suspension, acidification, solids removal, neutralization and product recovery steps.

11 Claims, No Drawings

PURIFICATION OF N-SUBSTITUTED AMINOBENZALDEHYDES

BACKGROUND

The production of high purity N-substituted aminobenzaldehydes is difficult because of the low yield of the product-forming reaction and the problems encountered in separating the benzaldehyde product from by-products present in the reaction mixture. These substituted benzaldehydes have utility in that they can impart dispersant properties to viscosity improvers.

INVENTION

It has been discovered that certain substituted aminobenzaldehydes can be effectively purified—i.e., separated from materials, such as reaction mixtures—containing them, via formation of aqueous suspension, acidification, separation of water insolubles, and neutralization steps.

In one embodiment, the following process is employed:

(1) suspension of crude dimethylaminobenzaldehyde (DMAB) in aqueous medium;

(2) acidification of suspended DMAB with HCl, to solubilize the DMAB but not the impurities present;

(3) filtration to remove water insoluble impurities;

(4) neutralization with caustic to a final pH of 7.0 to give a precipitate with high product yield and purity; and (5) recovery of the precipitate of step (4).

OBJECTS OF THE INVENTION

It is an object of the invention to provide a process for the purification of N-substituted aminobenzaldehydes.

It is another object of the invention to provide a purification process in which the recovery of N-substituted aminobenzaldehydes is aided by a particular sequence of chemical and physical steps.

Advantages

The process of the invention has several advantages over known processes of recovering the subject benzaldehydes. Typical methods employed in the past have included high vacuum (0.5 mm Hg) distillation, or a two-step recrystallization (first from water, then from organic solvent, e.g., cyclohexane).

Furthermore, the purification process of the invention yields a crystalline precipitate which is readily separable by inexpensive techniques such as filtration.

Other aspects and advantages of the invention will become apparent from a reading of applicant's specification and claims.

DESCRIPTION OF THE INVENTION

Aminobenzaldehydes

The aminobenzaldehydes which are recovered in accordance with the invention are N-substituted benzaldehydes conforming to the general formula:

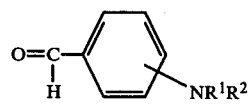

where at least one of $R^1$ and $R^2$ is not hydrogen, and $R^1$ and $R^2$ are selected independently from hydrogen and organic moieties containing from about 1 to about 10, and preferably from about 1 to about 6 carbon atoms. Typically, $R^1$ and $R^2$ are both alkyl groups. It is preferred that $R^1$ and $R^2$ be the same and that they be methyl, ethyl, or propyl groups. p-Dimethylaminobenzaldehyde is a highly preferred aminobenzaldehyde.

The N-substituted aminobenzaldehydes to be purified in accordance with the invention can be produced via a variety of known reactions. One typical reaction is the production of p-dimethylaminobenzaldehyde by the formylation of N,N-dimethylaniline with hexamethylenetetramine in the presence of an organic acid, preferably acetic acid, as shown in Polish patent No. 57,927, whose disclosure is incorporated herein by reference.

Other suitable reactions are described in *Organic Syntheses* Coll. Vol. 1, 214–217 (1941) and *Organic Synthesis*, 33, 27–29 (1953), whose disclosures are incorporated herein by reference.

Generally the crude aminobenzaldehydes which can be purified by the process of this invention will be in the form of relatively dry water-washed solids free of significant amounts of easily volatilized materials other than water.

Purification Process

The purification process of the invention comprises five steps:

(1) suspension of the crude aminobenzaldehyde in aqueous medium, (2) treatment of the crude aminobenzaldehyde with acid, (3) separation of insolubles from the acidified material, and (4) neutralization of the soluble product from step (3) with base to form solids, and (5) recovery of the solids of step (4).

The suspension step, step (1), generally involves the addition of from about 5 to about 15 parts by volume of water or other aqueous medium to about 1 part by weight of crude aminobenzaldehyde. Preferably, about 10 volumes, e.g., milliliters, of water per gram of DMAB will be employed. Any suitably proportionate relationship of volume to weight, e.g., liters per kilogram or milliliters per gram, is operable. Mixtures of aqueous media can be employed.

The acidification step, step (2), involves the solubilizing of the crude aldehyde in acid. The amount of acid used is not critical so long as there is enough acid present to dissolve the desired product, i.e., the aldehyde. Usually the molar ratio of acid to aminobenzyaldehyde will be about 5:1 to about 1:1, with about 3:1 to about 1.5:1 preferred.

The type of acids operable herein include organic and inorganic substances. However, it is important that the acid be one in which the aminobenzaldehyde to be purified is sufficiently soluble that it remains in acid solution during the subsequent filtration step. While acetic and sulfuric acids do not produce the desired solubilization in step (2), hydrochloric acid and other so-called strong acids are operable. Mixtures of acids can be used.

The separation of insolubles is carried out conventionally. For example, filtration or centifugation can be used. While no particular apparatus need be employed, gravity or vacuum filtration can be conveniently carried out using filter paper or sintered glass filter elements or the like.

The neutralization step requires the addition of sufficient base, or caustic, to the product of step (3) to yield a pH of about 7. Suitable bases for the neutralization step include alkali metal oxides, hydroxides, and the like. Preferably, NaOH is employed. Most preferably NaOH is added as a solution containing about 30 weight percent NaOH. This solution gives the optimum recovery of high purity product. Mixtures of bases can be used.

Upon standing or after suitable temperature and/or pressure variation, a crystal fraction rich in the desired aminobenzaldehyde is attained.

The purified crystal fraction is recovered from the basic liquor via conventional techniques, e.g., filtration, centrifugation, and the decantation of liquid layer and the like.

Other conventional recovery techniques can be employed before, during, or after the 5-step process of the invention in order to improve product recovery.

EXAMPLES

Example I

N,N-dimethylaniline (DMA), hexamethylenetetramine (HMTA), acetic acid (HOAc) and water ($H_2O$) were all charged to a 1 liter stainless steel Magnedrive Autoclave Engineers stirred tank reactor. The autoclave was then flushed with a nitrogen purge, sealed with a 10–20 psig $N_2$ cap, and subsequently heated to 135° C. and maintained at that temperature and autogeneous pressure for about 1 hour. All runs and the particular molar quantity of reactant, based upon 1 mole of DMA are given below. Product yields were determined either by gas chromatographic analysis of the unhydrolyzed reaction product (employing cyclohexylbenzene as internal standard), or by acid hydrolysis of the Schiff's base product with 3 volumes of dilute acid per volume of reactor effluent followed by filtration to collect product.

TABLE I

| | Mole Ratio of Reagents[a] | | | DMA Conv, mol % | Sel. to DMAB, mol % | Yield of DMAB, mol % |
|---|---|---|---|---|---|---|
| Run | HMTA | HOAc | $H_2O$ | | | |
| 1 | 1.5 | 7.0 | 3.5 | 100 | 71 | 71 |
| 2 | 1.5 | 7.0 | 3.3 | 100 | 73 | 73 |
| 3 | 1.5 | 2.8 | 3.3 | 55 | 59 | 32 |
| 4 | 1.5 | 4.2 | 3.3 | 69 | 62 | 43 |
| 5 | 1.5 | 5.6 | 3.3 | 88 | 66 | 58 |
| 6 | 1.5 | 7.0 | 3.3 | 100 | 72 | 72 |

[a]Relative to 1 mole of DMA

The data demonstrate the preparation of the desired product p-dimethylaminobenzaldehyde (DMAB) by the method of Polish patent No. 57,927.

Example II

The solubility of crude dimethylaminobenzaldehyde (DMAB) in a variety of solvents was tested as follows: 0.5 g of crude (~70%) DMAB and 2 mL of solvent were placed in a test tube and shaken.

TABLE II

| Solvent | DMAB Soluble |
|---|---|
| Water | No |
| Methyl ethyl ketone | Yes |
| Cyclohexylbenzene | Yes |
| Anisole | Yes |
| Methylacetate | Yes |
| Dimethylcyclohexane | Yes |

TABLE II-continued

| Solvent | DMAB Soluble |
|---|---|
| Methanol | Yes |
| Cyclohexane | No |
| n-Propyl alcohol | Yes |
| i-Propyl alcohol | Yes |
| Acetonitrile | Yes |

Example III

Based on the above solubility tests, purification of crude DMAB was attempted by using a solvent-nonsolvent combination as follows. 2 g of crude (~70%) DMAB was dissolved in 10 mL of methanol by mixing together in a small beaker. Then a nonsolvent for DMAB was added slowly. Upon addition of water as nonsolvent, the solution became cloudy, followed by formation of an oil which slowly settled out. Upon addition of cyclohexane to the methanol solution of crude DMAB, an oil formed immediately, without any evidence of crystal formation.

Example IV

The solubility of crude dimethylaminobenzaldehyde (DMAB) in the presence of several acids was tested. 2 g of crude (~70%) DMAB and 20 mL of water were mixed in a small beaker. Acid was added with stirring until the two phases (water-DMAB) became miscible.

TABLE III

| Acid | Wt. Added, g | Soluble |
|---|---|---|
| Glacial $CH_3CO_2H$ | 5.0 | No |
| 25% $H_2SO_4$ | 5.0 | No |
| Con. $H_3PO_4$ | 4.0 | No |
| Con. HCl | 2.8 | Yes |

Example V

Based on the above acid solubility tests, crude DMAB and water were combined, a sufficient amount of concentrated (37%) HCl was added to cause the two-phases to become miscible (i.e., solid DMAB dissolved), the resultant solution was filtered to remove insoluble oils, then base was added to precipitate purified DMAB. Purity of DMAB was determined by dissolving purified DMAB in methanol, then analyzing by gas chromatography.

The effect of several variables on product purity and recovery were investigated, such as the ratio of crude DMAB to volume of water used for solution, the type of base employed for neutralization, the ultimate pH attained upon neutralization, and the concentration of base solution employed.

TABLE IV

| Crude* DMAB, g | $H_2O$, mL | HCl**, g | Base***, g | Final pH | Product % Recovered | % Purity |
|---|---|---|---|---|---|---|
| 2.0 | 10 | 2.5 | $NH_4OH$, 2.25 | 7.0 | 57 | 14 |
| 2.0 | 20 | 2.75 | $NH_4OH$, 2.7 | 7.0 | 57 | 15 |
| 2.0 | 20 | 2.75 | $NH_4OH$, 3.0 | 9.0 | tar | |
| 2.0 | 20 | 2.75 | $NH_4OH$, 2.5 | 5.5 | 43 | 10 |
| 2.0 | 10 | 2.75 | 30% NaOH, 3.0 | 7.0 | 86 | 17 |
| 2.0 | 20 | 2.85 | 30% NaOH, 3.5 | 7.0 | 93 | 17 |
| 2.0 | 20 | 2.85 | 30% NaOH, 3.7 | 8.5 | tar | |
| 2.0 | 30 | 2.95 | 30% NaOH, 3.7 | 7.0 | 86 | 16 |

TABLE IV-continued

| Crude* DMAB, g | H₂O, mL | HCl**, g | Base***, g | Final pH | Product % Recovered | % Purity |
|---|---|---|---|---|---|---|
| 2.0 | 20 | 2.8 | 15% NaOH, 7.0 | 7.0 | 79 | 92 |
| 2.0 | 20 | 2.8 | 50% NaOH, 2.0 | 7.0 | 64 | 91 |

*70% Purity
**Concentrated HCl (37%)
*** Concentrated NH₄OH (28%), NaOH solutions are expressed as wt %.

These results indicate that optimal recovery of purified DMAB is obtained with: (1) approximately 10 mL of water per gram of crude DMAB; (2) an ultimate pH upon basification of 7; and (3) 30 wt % NaOH for neutralization of solubilized crude DMAB. Under these conditions, greater than 90% recovery of high purity DMAB (e.g., 97%) can be obtained.

Reasonable variations, such as those which would occur to the skilled artisan, can be made herein without departing from the scope of the invention.

I claim:

1. A process for recovering high purity N-substituted aminobenzaldehydes, from a material containing such compounds comprising the steps of:
   (1) suspending crude aminobenzaldehyde in aqueous medium,
   (2) contacting the product of step (1) with acid,
   (3) separating insolubles from the product of step (2),
   (4) neutralizing the soluble product of step (3) to form a precipitate, and
   (5) recovering the precipitate of step (4).

2. The process of claim 1 wherein step (1) is carried out via the addition of about 5 to 15 parts by volume of aqueous medium per part by weight of crude aminobenzaldehyde.

3. The process of claim 2 wherein there is added about 10 parts by volume of aqueous medium per 1 part by weight of crude aminobenzaldehyde.

4. The process of claim 2 wherein step (4) is carried out via addition of a base to the product of step (3).

5. The process of claim 4 wherein the base employed is at least one selected from the group consisting of the oxides and hydroxides of alkali metals.

6. The process of claim 5 wherein the base employed contains an alkali metal hydroxide.

7. The process of claim 6 wherein the base contains sodium hydroxide.

8. The process of claim 2 wherein the N-substituted aminobenzaldehyde is p-dimethylaminobenzaldehyde.

9. The process of claim 7 wherein the aminobenzaldehyde is p-dimethylaminobenzaldehyde.

10. The process of claim 2 wherein the acid is HCl.

11. The process of claim 9 wherein the acid is HCl.

* * * * *